United States Patent [19]
Kuroiwa et al.

[11] Patent Number: 4,717,659
[45] Date of Patent: Jan. 5, 1988

[54] NOVEL METHOD FOR DETERMINING CHOLINESTERASE ACTIVITY

[75] Inventors: Katsumasa Kuroiwa; Katsuhiro Katayama; Katsuyuki Takabayashi, all of Koriyama; Takeshi Nagasawa, Urawa, all of Japan

[73] Assignee: Nitto Boseki Co., Ltd., Fukushima, Japan

[21] Appl. No.: 731,069

[22] Filed: May 6, 1985

[30] Foreign Application Priority Data

May 10, 1984 [JP] Japan ................................ 59-93547

[51] Int. Cl.$^4$ ............................................. C12Q 1/46
[52] U.S. Cl. ................................................... 435/20
[58] Field of Search ................................ 435/20, 810

[56] References Cited

U.S. PATENT DOCUMENTS 4,565,780   1/1986   Motonaga et al. .................. 435/20

FOREIGN PATENT DOCUMENTS 0060059    9/1982   European Pat. Off. ............. 435/20
0155825    9/1985   European Pat. Off. .
2018988   10/1979   United Kingdom .

OTHER PUBLICATIONS

S. Clausen et al., "Sep'n of Aromatic Choline Esters by High-Perf. Liquid Chromatog.," J. Chromatog., vol. 260 (1983), pp. 193–199.

Consera I. Nissui Pharmaceutical Co. Ltd., Tokyo, Japan.
Precipath E, Boehringer Mannheim, Mannheim, West Germany Primary Examiner—Robert J. Warden
Assistant Examiner—Randall E. Deck
Attorney, Agent, or Firm—Bert J. Lewen; Henry Sternberg

[57] ABSTRACT

In a method for determining cholinesterase (hereinafter referred to as ChE) activity, the improvement comprising by using, as a substrate, a protocatechuoylcholine derivative represented by the general formula (I),

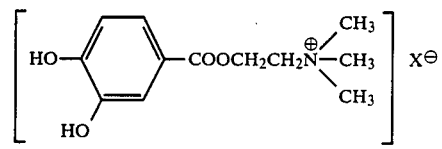

(wherein X is a halogen atom).

The method for determining ChE activity according to the present invention is free from defects of the conventional methods, has many advantages and characteristics, permits accurate and simple determination of ChE activity, and can sufficiently contribute to determination of ChE activity in daily clinical examinations.

7 Claims, 15 Drawing Figures

OPTIMUM pH OF CHOLINESTERASE (ChE)

NOVEL METHOD FOR DETERMINING CHOLINESTERASE ACTIVITY

FIELD OF THE INVENTION

This invention relates to a method for determining cholinesterase activity, characterized by using, as a substrate, a protocatechuoylcholine halide derivative represented by the general formula (I):

wherein X is a halogen atom.

DESCRIPTION OF THE PRIOR ART

There have heretofore been reported various methods for determining cholinesterase (hereinafter referred to as ChE) activity in serum using a synthesized substrate, and some of them have been made practicable for daily clinical examinations. However, these determination methods involve various defects and problems, and these disadvantages are responsible for the inaccuracy of the resulting determined value. Examples of the heretofore well-known determination methods include (a) gas analysis method, (b) pH meter method, (c) pH-indicator colorimetry, (d) thiocholine color formation method, (e) enzymatic method, (f) UV method, etc.

(a) The gas analysis method [R. Ammon: Pflügers Arch. Ges Physiol., 233, 487 (1933)] comprises using acetylcholine as a synthesized substrate, bringing acetic acid produced by the enzymatic action of ChE into contact with sodium hydrogen carbonate, and quantitatively determining the carbon dioxide gas produced. This method is disadvantageous, for example, in that since its operations are troublesome, it cannot deal with many samoles.

(b) The pH meter method [H. O. Michel: J. Lab. Clin. Med., 34, 1564 (1949)], like the gas analysis method, comprises measuring a pH change due to acetic acid produced by the enzymatic action of ChE by means of a pH meter. This method involves practical problems of, for example, accuracy of pH meter, inability to deal with many samples, and the like.

(c) The pH-indicator calorimetry, unlike the pH meter method, comprises measuring a pH change due to acetic acid produced by ChE in terms of the molecular absorbance of the indicator. As the indicator, there are used phenol red [Hiroshi Takahashi and Susumu Shibata, IGAGU-TO-SEIBUTSUGAKU (Medicine and Biology), 20, 96, (1959)], bromothymol blue [H. G. Biggs, et al., Amer. J. Clin. Path., 30, 181, (1958)], m-nitrophenol [Tadahide Sasaki, RINSHO-BYORI (Clinical Pathology), 12, 555, (1964)], etc. This method comprises simple operations and can deal with many samples, but it is pointed out that this method is disadvantageous, for example, in that the reaction time is long and in that during the reaction, the pH is not constant and is not sufficiently reproducible at low and high values.

In the case of the above-mentioned methods using acetylcholine as a substrate, the substrate itself also is disadvantageous because acetylcholine tends to undergo nonenzymatic hydrolysis and has no sufficient substrate specificity.

(d) The thiocholine method [P. Garry, J. Clin. Chem., 11 (2), 91 (1965)] uses acetylthiocholine, propylthiocholine, butylthiocholine or the like as a substrate. These substrates yields thiocholine by the enzymatic reaction of ChE, and this thiocholine reacts with,5,5'-dithiobis-2-nitrobenzoic acid (DTNB) to produce a yellow color. Said method comprises measuring this yellow color by means of a colorimeter. This method is advantageous, for example, in that it is excellent in reactivity, has a high sensitivity, comprises simple operations, can deal with many samples, and permits employment of an initial velocity method. However, it is disadvantageous, for example, in that it is seriously affected by bilirubin in serum because of the yellow coloration and unavoidably affected by compounds having a thiol group such as glutathione, and in that the instability of the substrate itself is a problem. These disadvantages are responsible for errors of determined values.

(e) The enzymatic method comprises using benzoylcholine [Hiroaki Okabe et al., RINSHO-BYORI (Clinical Pathology), 25, 751, (1977)], orthotoluoylcholine [Japanese Patent Application Kokai (Laid-Open) No. 138533/79] or the like as a substrate, converting choline produced by the enzymatic action of ChE into betaine by cholineoxidase, and allowing hydrogen peroxide produced at this time to produce color by its oxidative condensation reaction with 4-aminoantipyrine, phenol or the like in the presence of peroxidase. In this method, since the coloration is red, there is not interference by bilirubin in serum, and many samples can be dealt with. However, since phenol or 4-aminoantipyrine used as a reagent for the color-producing system competitively inhibits ChE, the amount of these reagents used is greatly limited, so that sufficient color production is difficult. In general, a determination method via hydrogen peroxide is unavoidably affected not only by bilirubin in serum, reducing substances such as ascorbic acid and the like, etc. but also by choline produced by decomposition of phospholipids or the like. The employment of benzoylcholine as a substrate involves various problems, for example, its nonenzymatic hydrolyzability which causes troubles.

(f) The UV method includes two kinds of methods, and one is a method of W. Kalow using benzoylcholine as a substrate [W. Kalow and K. Genet, Can. J. Biochem. & Physiol., 35, 339 (1957)], while the other is a method using p-hydroxycholine [Japanese Patent Application Kokai (Laid-Open) Nos. 110198/82 and 129999/83] as a substrate. The former comprises following a decrease in amount of the substrate caused by its hydrolysis by the enzymatic action of ChE at a determination wave length of 240 nm. The principle of determination of this method is simple and plain because the decrease of the substrate is directly determined. However, this method is disadvantageous, for example, in that since the determination wave length is 240 nm, interference by serum components tends to occur, that since benzoylcholine, i.e., the substrate causes substrate inhibition, the substrate concentration of the reaction solution is limited, resulting in a narrow range of linearity, and that since nonenzymatic hydrolysis of benzoylcholine tends to occur, the reaction is not carried out at the optimum pH of ChE. The latter comprises using p-hydroxybenzoylcholine as a substrate, allowing p-hydroxybenzoate hydroxylase to act on p-hydroxybenzoic acid produced by the enzymatic action of ChE, in the presence of the coenzyme NADPH [nicotinamide adenine dinucleotide phosphate (reduced form)], and determining and following, at a wave length of 340 nm, a decrease of absorbance at the time of oxidation of NADPH into NADP by the enzymatic action. This method is an excellent method for determining ChE activity which makes it possible to carry out the reaction at an almost optimum pH, permits removal of the defects of the hydrogen peroxide color-producing system, namely, influence of bilirubin, reducing substances such as ascorbic acid and the like, etc. and interference by choline produced by decomposition of phospholipids, is free from the defects of the thiocholine method, and is suitable for an autoanalyzer capable of dealing with many samples. However, since NADPH, the coenzyme used, is an expensive reagent and is poor in stability, it is difficult to control while being kept at a definite quality. Further, in this method, p-hydroxybenzoate hydroxylase, protocatechuate 3,4-dioxygenase or the like is used as a reagent enzyme in the determination, and moreover the principle of determination is considerably complicated as compared with the former determination method; therefore there are many factors which produce an error of the resulting determined value. As to a method for determining ChE activity, determination of pseudo-cholinesterase activity is also important. However, the latter determination method is seriously affected by sodium fluoride and hence is not suitable for determining pseudo-cholinesterase activity.

As described above, the conventional methods for determining the enzymatic activity of ChE involve various problems, which are responsible for errors of measured values. In order to remove the defects of various heretofore well-known determination methods, the present inventors have devoted themselves to research and have consequently invented a novel method for determining serum ChE activity using, as a substrate, protocatechuoylcholine iodide (hereinafter referred to as PCI) which is one of the compounds represented by the general formula (I).

SUMMARY OF THE INVENTION

An object of the present invention is to provide a novel method for determining cholinesterase activity.

Another object of the present invention is to provide choline derivative which can be used as the substrate in the method.

DETAILED DESCRIPTION OF PREFERRED EMBODIMENTS

Figure 2:
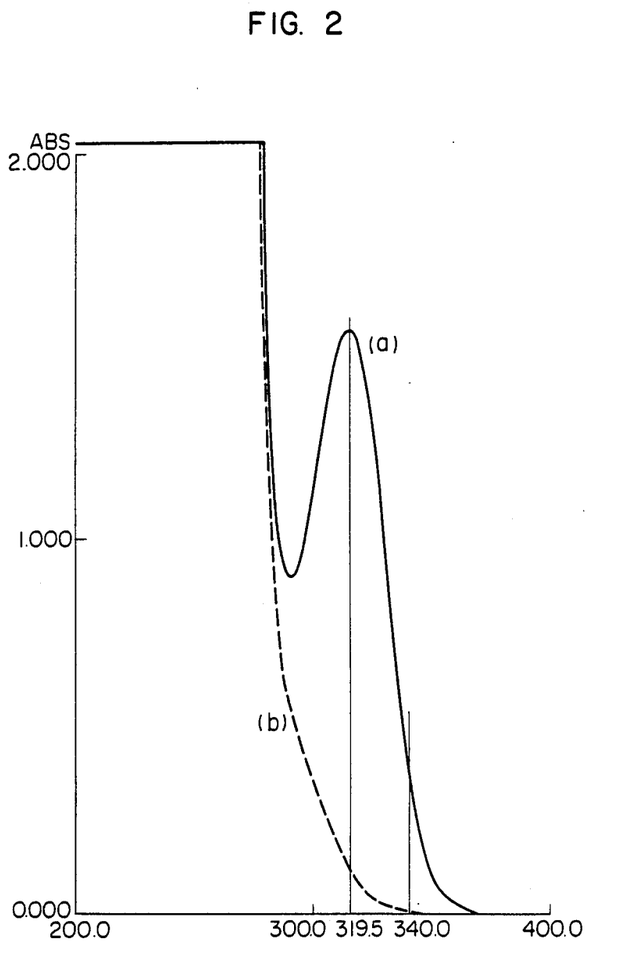
FIG. 2 shows UV spectra [in a 50 mM barbital buffer solution LpH 8.5 )] of (a) protocatechuoylcholine iodide (concentration: 100 μM) and (b) protocatechuic acid (concentration: 100 μM).

UV spectra of PCI and protocatechuic acid are shown in FIG. 2. On hydrolysis by the action of ChE, PCI gives choline and protocachuic acid. Choline has no UV absorption at a wave length longer than 300 nm. Protocatechuic acid has almost no UV absorption at a wave length longer than 340 nm. Therefore, when PCI is used as a substrate for determining ChE activity and the reaction is followed at a determination wave length of 340 to 360 nm, a decrease in amount of the substrate PCI can accurately be followed. In the above-mentioned UV method of W. Kalow, the determination wave length is 240 nm and hence serious interference by blood components occurs in initial absorptions. On the other hand, no serious interference occurs at the determination wave length of 340 to 360 nm of this invention, so that it is easy to determine the optimum determination conditions. The substrate PCI is very stable to nonenzymatic hydrolysis. For example, hydrolysis hardly occurred under the conditions of 37° C. in a 50 mM barbital buffer solution having a pH of 8.5 for 90 minutes (see FIG. 6). This result indicates that nonenzymatic hydrolysis is negligible in the determination. As a buffer for keeping the pH constant, there can be used barbiturates, phosphates, pyrophosphates, glycine, glycylglycine, tris(hydroxymethyl)aminomethane, etc. Any buffer other than those described above can be used so long as it can retain its buffer capacity in the pH range from 7.5 to 10.0.

The Km value of PCI for ChE is substantially the same as that of benzoylcholine and is $2.6 \times 10^{-5}$ mol/liter in a 50 mM tris-maleic acid buffer solution (pH 8.2) and $5.88 \times 10^{-5}$ mol/liter in a 50 mM barbital buffer solution (pH 8.5). Since the Km value of PCI is sufficiently small, the reaction can be carried out at sufficient substrate concentration in the reaction system of the determination method of this invention, and the range of linearity with the lapse of time is enlarged, so that the determination can sufficiently be carried out for a high unit of the activity.

Figure 5:
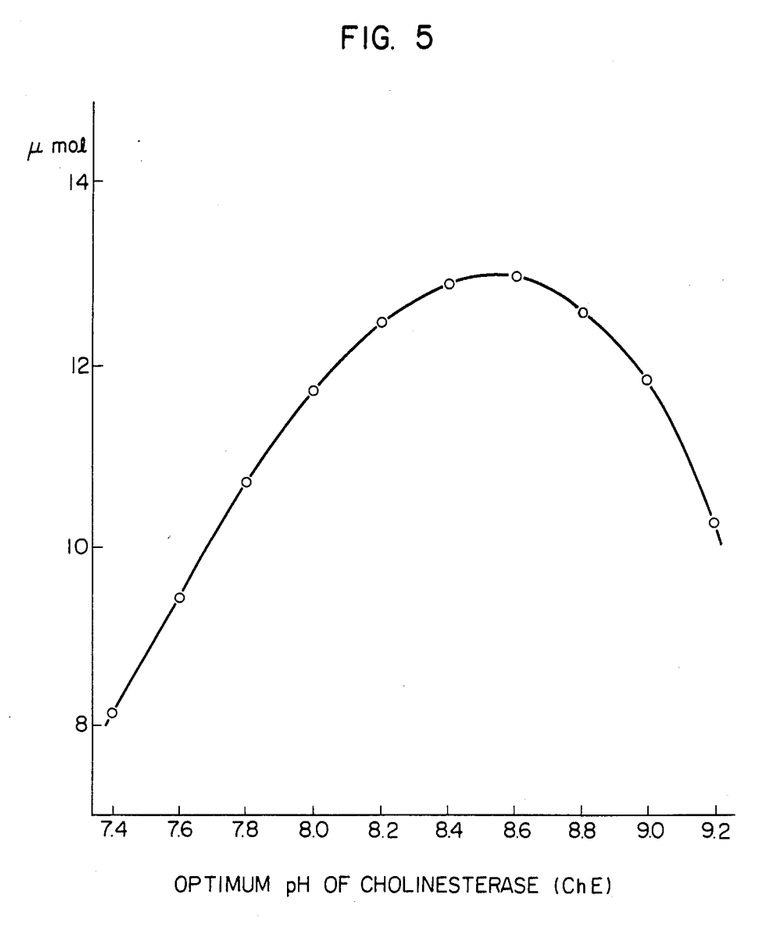
FIG. 5 shows the optimum pH of ChE.

When PCI is used as a substrate, the optimum pH of ChE was 8.5 to 8.6 in a 50 mM barbital buffer solution (see FIG. 5). As described above, PCI is stable to noenzymatic hydrolysis at pH 8.5, and hence the determination method of this invention makes it possible to carry out the reaction at the optimum pH of ChE.

Figure 14:
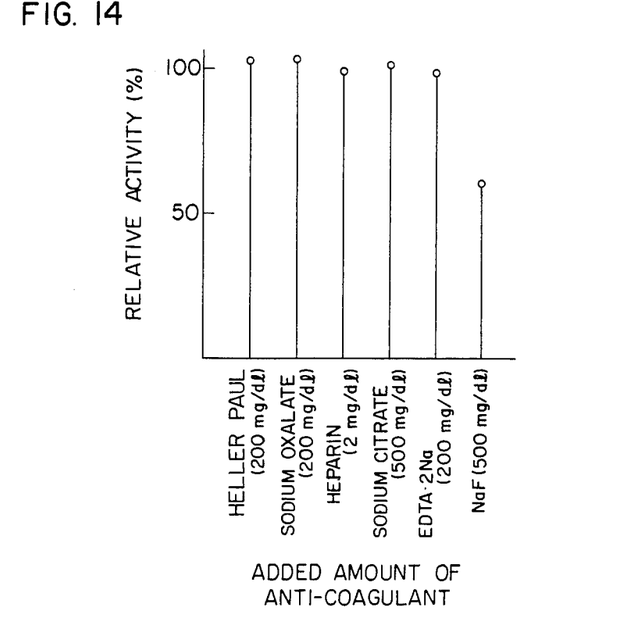

It is as described above that when the coexisting substances in a sample affect the resulting determined value, they cause an error of the determined value. The determination method of this invention is hardly affected by the coexisting substances also from the viewpoint of its principle. Coexisting substances, for example, up to 20 mg/dl of ascorbic acid, up to 20 mg/dl of uric acid, up to 500 mg/dl of glucose, up to 200 mg/dl of hemoglobin, up to 5 g/dl of albumin, up to 20 mg/dl of bilirubin, and up to 50 mg/dl of glutathione (reduced form) caused no trouble in addition tests (see FIGS. 7 to 13). Further, no trouble was caused also in addition tests on EDTA.2Na (ethylenediamine tetraacetic acid disodium salt), citrate, heparin, oxalate, dihydrogenoxalic acid, and the like as anti-coagulants (see FIG. 14). The determination method of this invention is hardly affected by the coexisting substances and is an excellent method for determining cholinesterase activity in which the causes of error of determined value in the heretofore well-known determination methods are greatly removed.

As cholinesterases, there are known two kinds, namely, pseudo-cholinesterase existing in serum and true-cholinesterase existing in erythrocyte. The one whose activity is usually determined in a clinical examination is pseudo-cholinesterase in serum, but since serum is contaminated with true-cholinesterase in some cases, a subtrate which reacts selectively with pseudo-cholinesterase alone is preferable. PCI used in the method of this invention is a substrate having a very high specificity which reacts well with pseudo-cholinesterase but hardly reacts with true-cholinesterase.

In the fields of surgery and psychiatry, an examination for abnormal pseudo-cholinesterase is important from the viewpoint of the relationship between anesthetics and pseudo-cholinesterase. The determination method of this invention is simple and plain with regard to the reaction mechanism and hence is very suitable as a method of examination for abnormal pseudo-cholinsterase.

The method for determining ChE activity of this invention is, as described above, free from the various problems of the conventional methods. The advantages of this invention are as described below.

(1) The reaction mechanism of the determination system is simple and plain, and there are very few causes of error in the determined value.

(2) Since PCI used as a substrate is stable to nonenzymatic hydrolysis and oxidation, the reproducibility of the determined value is very good.

(3) PCI has a high substrate specificity for pseudo-cholinesterase.

(4) Since none of enzymes and coenzymes for redox systems and reagents for coloration systems are used in addition to the substrate PCI, the method of this invention is inexpensive.

(5) As described above, said method is hardly affected by sample components such as bilirubin, ascorbic acid, glutathione and the like and anti-coagulants.

(6) Since it is unnecessary to employ a sample blank for each sample, the determination can be carried out easily and rapidly, so that many samples can be dealt with.

(7) Examination for abnormal pseudo-cholinesterase is possible.

(8) Since PCI is stable, the reaction can be carried out at the optimum pH (8.5 to 8.6) for ChE.

(9) The determination is possible up to a high unit of the activity.

As described above, the method for determining ChE activity of this invention is free from the defects of the conventional methods, has many advantages and characteristics, permits accurate and simple determination of ChE activity, and can significantly contribute to the determination of ChE activity in daily clinical examinations.

This invention is further explained below in more detail with reference to Referential Examples and Examples, which are not by way of limitation but by way of illustration.

REFERENTIAL EXAMPLE 1

Synthesis Process of Protocatechuoylcholine Iodide

In 71 ml of 2.73 N NaOH was dissolved 10 g of protocatechuic acid, after which the resulting solution was cooled to 0° to 5° C. and 22 ml of carbobenzoxy chloride was added dropwise with vigorous stirring. At the same time, 2.73 N NaOH was also added dropwise so as to maintain the pH at 9 to 10. The pH became constant in about 1 hour. Subsequently, the mixture thus obtained was subjected to reaction with stirring at room temperature for 3 hours. After completion of the reaction, the reaction mixture was adjusted to pH 2 with cold 5 N HCl and extracted with 200 ml of ethyl acetate and then 100 ml thereof, and the ethyl acetate layers were combined, thereafter washed with an aqueous sodium chloride solution, and then dried over anhydrous magnesium sulfate. Then, the solvent was distilled off under reduced pressure to obtain 25 g of an oily substance. The substance was recrystallized from ethyl acetate/n-hexane to obtain 9.2 g of O,O'-dicarbobenzoxyprotocatechuic acid. In 50 ml of ether was suspended 4 g of this product while preventing moistening, after which 2 g of phosphorus pentachloride was added in powder form, and the resulting mixture was subjected to reaction with stirring at room temperature for 5 hours. After completion of the reaction, the solvent was distilled off under reduced pressure to obtain 4.5 g of an oily substance. A solution of this substance dissolved in 20 ml of benzene was added dropwise to a solution of 2 ml of dimethylaminoethanol dissolved in 30 ml of benzene, with cooling to 5° to 10° C. After the addition, the resulting mixture was stirred overnight at room temperature to be subjected to reaction, and subsequently washed with water and then a saturated aqueous sodium chloride solution. The benzene phase was dried over anhydrous magnesium sulfate, and then the solvent was distilled off under reduced pressure to obtain 4.9 g of an oily substance. This substance was dissolved in 260 ml of ethanol, followed by adding thereto 2 g of palladium black, and catalytic reduction was carried out for 5 hours, after which the catalyst was filtered off and the ethanol was distilled off under reduced pressure to obtain 3 g of an oily substance. This substance was dissolved in 90 ml of acetone, followed by adding thereto a solution of 2 g of methyl iodide dissolved in ethyl acetate, and the resulting mixture was allowed to stand overnight at room temperature to deposit crystals. The crystals were collected by filtration, sufficiently washed with acetone, and then dried overnight over phosphorus pentaoxide under reduced pressure to obtain 2.5 g of protocatechuoylcholine iodide, a novel compound of this invention, m.p. 205°–209° C. These crystals gave a single spot (Rf=0.31) in a silica gel thin layer chromatography (n-butanol:acetic acid:water=4:1:2).

Elementary analysis values: for $C_{12}H_{18}NO_4I$ (M.W. 367.166): Found (%): C: 39.34; H: 5.07; N: 3.90. Calculated (%): C : 39.25 ; H: 4.94; N: 3.81.

Figure 1:
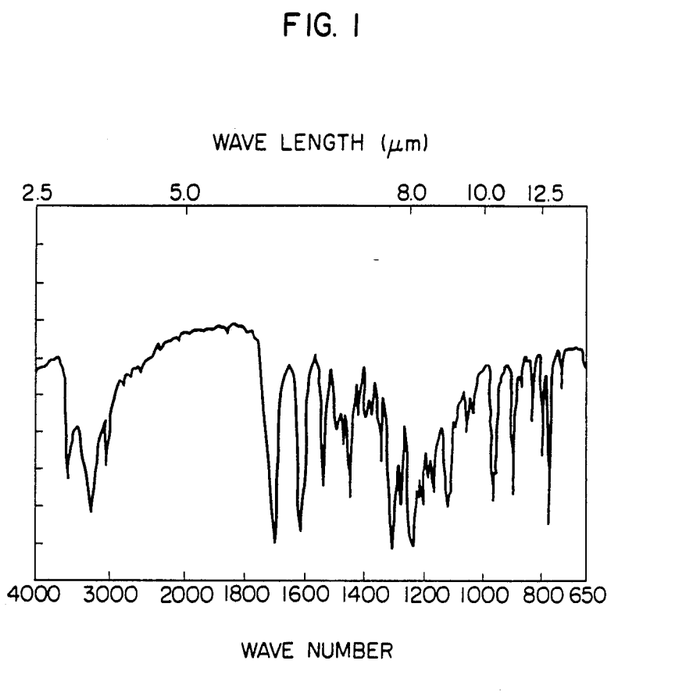
FIG. 1 shows an IR spectrum of protocatechuoylcholine iodide.

Their IR spectrum and UV spectrum are shown in FIG. 1 and FIG. 2, respectively.

EXAMPLE 1

Figure 3:
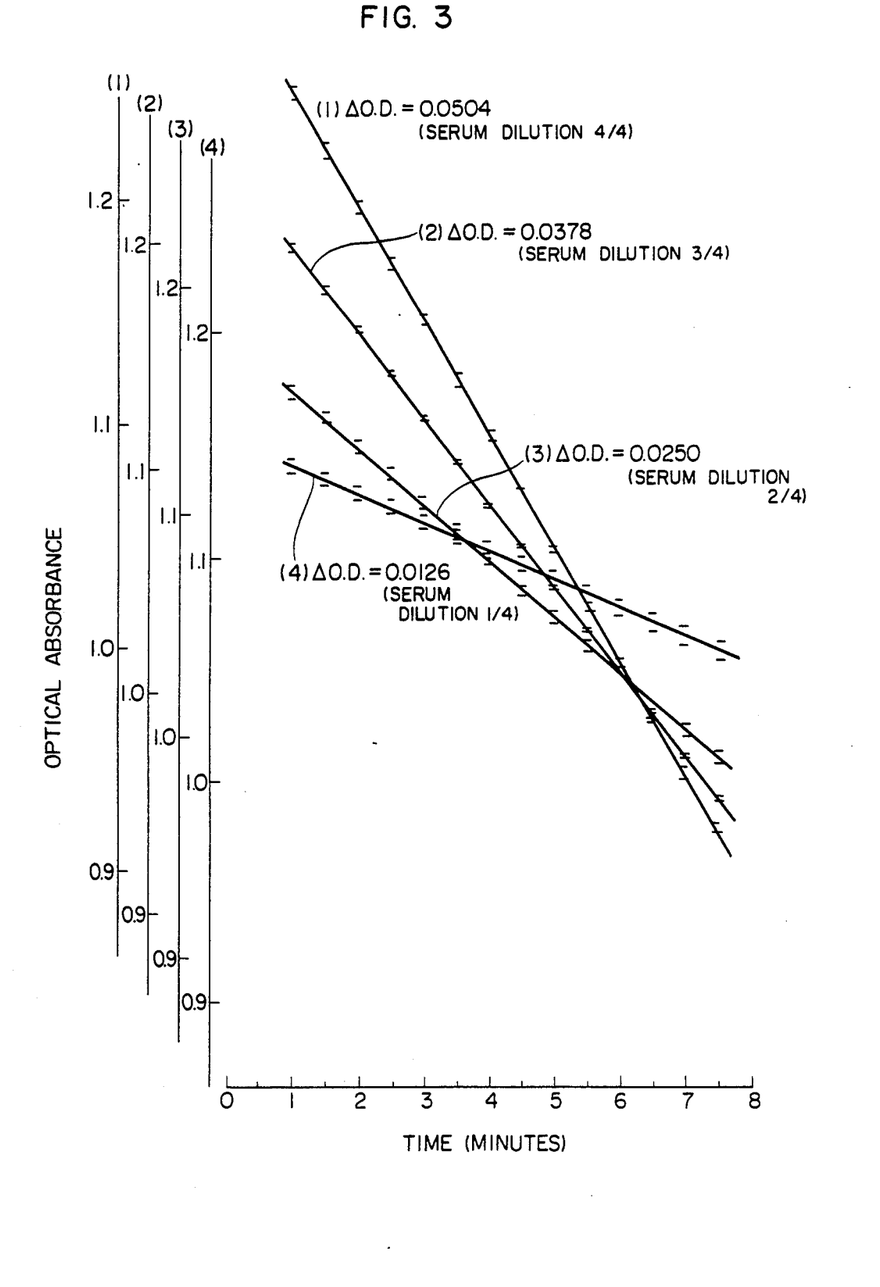
FIG. 3 shows a time course observed for diluted serum.
Figure 4:
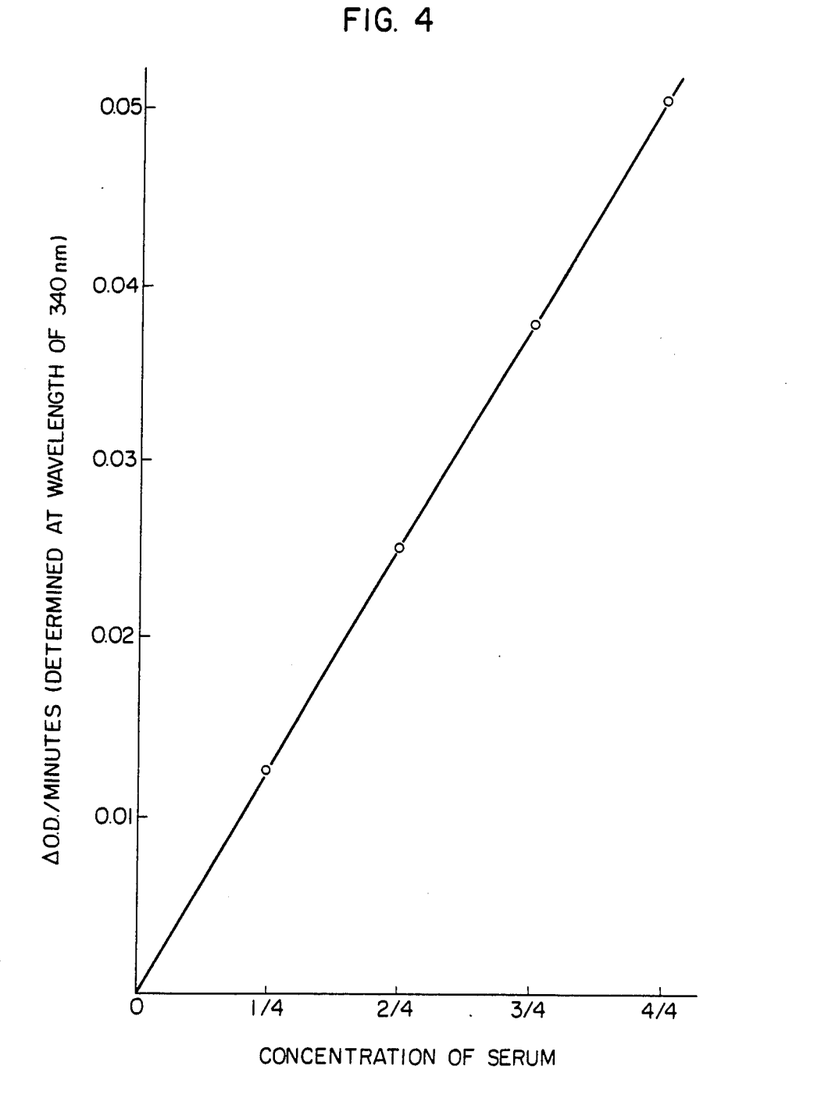
FIG. 4 shows the relationship between serum dilution and ΔO.D.

Method for Determining Serum ChE Activity (1) a 50 mM barbital buffer solution (pH 8.5, 25° C.)
(2) a sample
(3) a 6.3 mM substrate (PCI) solution To the 2.0 ml of the buffer solution of (1) was added 0.1 ml of the sample, and preheating was conducted at 37° C. for about 2 to 10 minutes. Thereto was added 0.1 ml of the substrate solution of (3) and the resulting mixture was quickly stirred and then subjected to determination by means of a spectroscope. The optical absorbance at 340 nm of the substrate was determined and followed with the lapse of time. FIG. 3 shows the results of measuring twice each of time courses for serum and diluted serum. The pH of the barbital buffer solution was adjusted at 25° C. As the serum, CONSERA I (manufactured by Nissui Pharmaceutical Co., Ltd.), and the serum was diluted with a 0.877% aqueous sodium chloride solution. As can be seen from FIG. 3, linearity was observed up to 8 minutes for each serum. The relationship between dilution of serum and ΔO.D. is shown in FIG. 4. The results obtained showed a perfectly straight line passing through the origin. This fact indicates that the ChE activity and ΔO.D. are proportional to each other, and that said novel method for determining ChE activity is practical and useful.

EXAMPLE 2

The pH of the buffer solution of (1) in Example 1 was varied from 7.4 to 9.2 and the optimum pH for ChE in said method was determined. This determination was carried out entirely according to Example 1 except for the pH of the buffer. The result obtained is shown in FIG. 5. Under these conditions, the optimum pH was 8.5 to 8.6.

EXAMPLE 3

Figure 6:
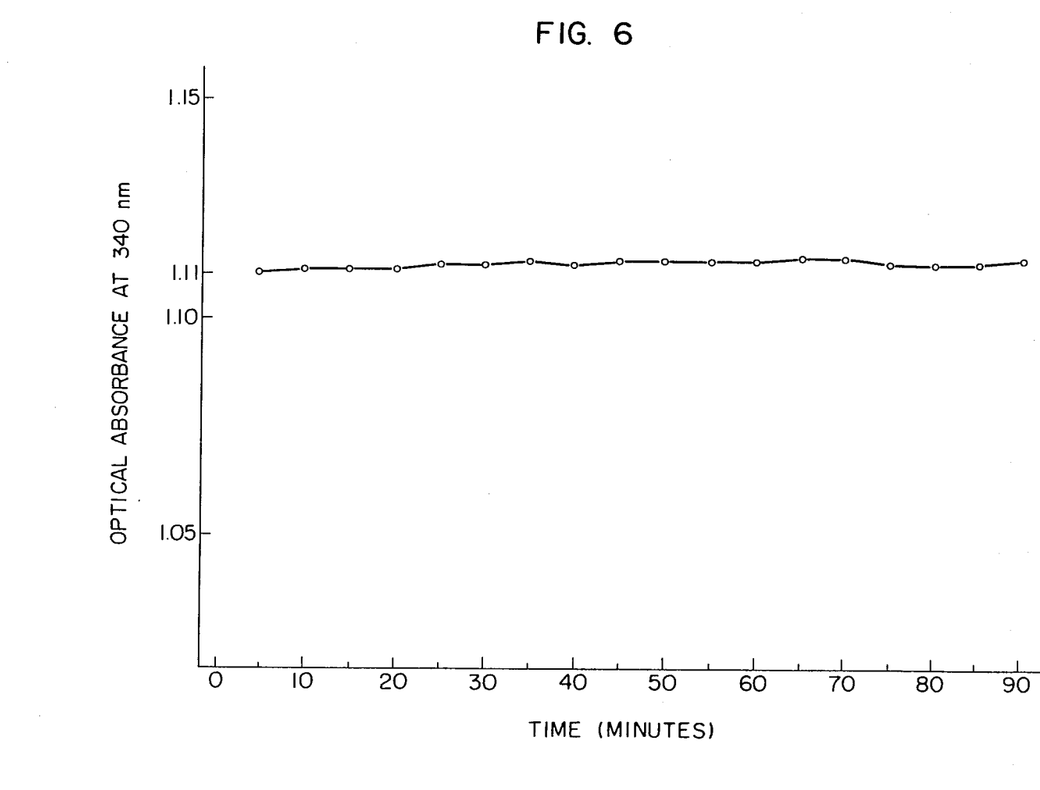
FIG. 6 shows the stability of a substrate to nonenzymatic hydrolysis.
Figure 7:
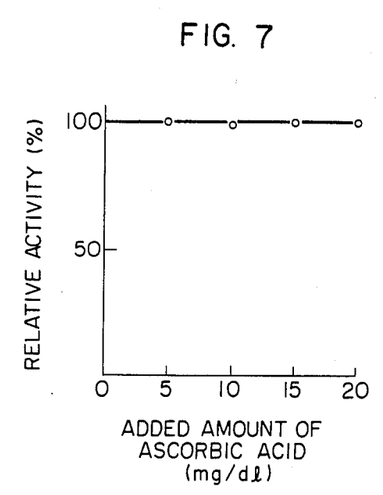
FIGS. 7 to 14 show the influences of additives.
Figure 8:
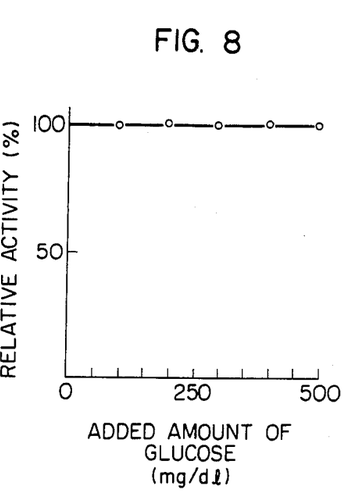
Figure 9:
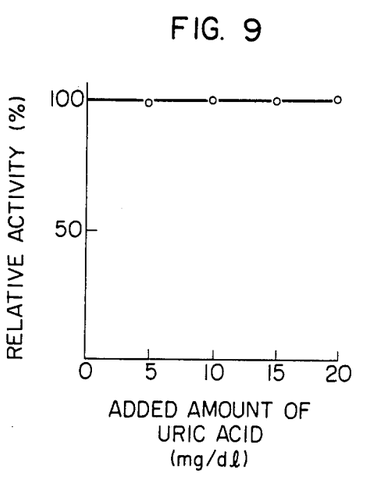
Figure 10:
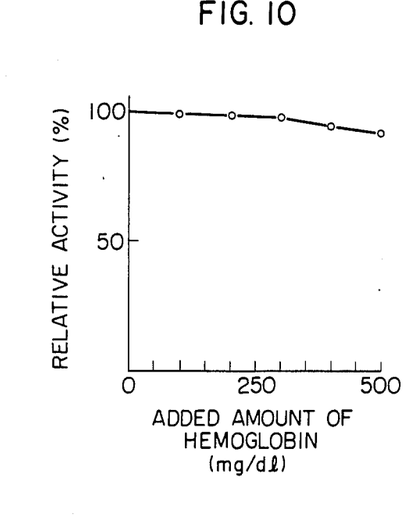
Figure 11:
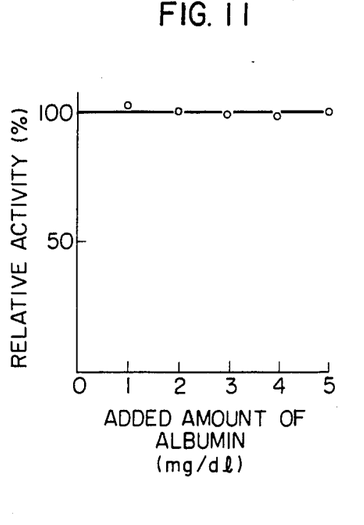
Figure 12:
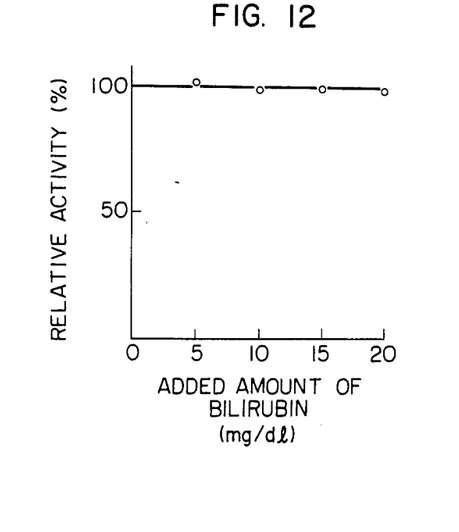
Figure 13:
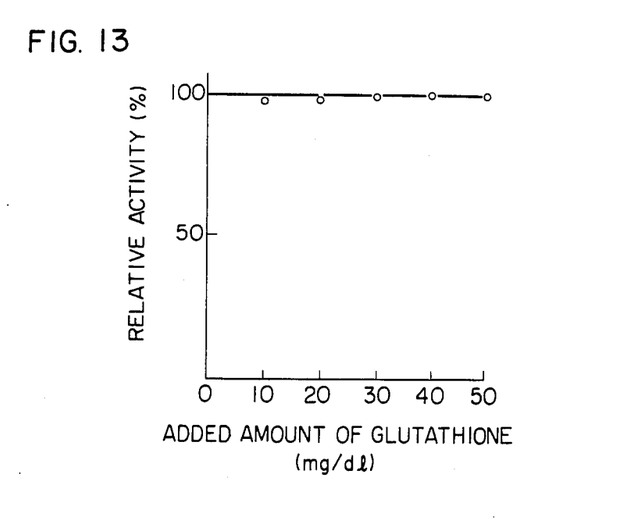

To 2.0 ml of the buffer of (1) in Example 1 was added 0.1 ml of the substrate solution of (3), and the resulting solution was placed in a heat insulating cuvette having a temperature of 37° C. The change of optical absorbance at a wave length of 340 nm was followed with the lapse of time, whereby the stability of the substrate to nonenzymatic hydrolysis was examined. As a result, the substrate was almost stable up to 90 minutes as shown in FIG. 6. Since the substrate PCI is stable at the optimum pH of 8.5, it is unnecessary to measure a reagent blank value for each sample.

EXAMPLE 4

The influence of the following additives in the reacation system was examined according to the determination method in Example 1.

| Additive | Added amount |
|---|---|
| (1) Ascorbic acid | 0-20 mg/dl |
| (2) Glucose | 0-500 mg/dl |
| (3) Uric acid | 0-20 mg/dl |
| (4) Hemoglobin | 0-500 mg/dl |
| (5) Albumin | 0-5 g/dl |
| (6) Bilirubin | 0-20 mg/dl |
| (7) Glutathione | 0-50 mg/dl |
| (8) Anti-coagulant | |
| Heller paul (a mixture of potassium oxalate with ammonium oxalate) | 200 mg/dl |
| Sodium oxalate | 200 mg/dl |
| Heparin | 2 mg/dl |
| Sodium citrate | 500 mg/dl |
| EDTA.2Na | 200 mg/dl |
| NaF | 500 mg/dl |

The determination results are shown in terms of relative activity (%) in FIGS. 7 to 14. As to hemoglobin, the relative activity was 97.3% in the case of its addition in an amount of 300 mg/dl, and hence the determination is possible up to about this amount. Since NaF is an inhibitor of pseudochloinesterase, determination of ChE activity by any method generally gives no accurate determined value in the presence of NaF. Therefore, from the result for NaF in FIG. 14, NaF cannot be used as an anti-coagulant in determining pseudo-cholinesterase activity.

EXAMPLE 5

Method for Determining Inhibitory Activity of Serum ChE (1) a 50 mM barbital buffer solution (pH 8.5, 25° C.)
(2) a sample
(3) a 6.3 mM substrate (PCI) solution
(4) a solution of 6.3 mM substrate (PCI) and 0.44 mM of dibucaine
(5) a solution of 6.3 mM substrate (PCI) and 220 mM NaF (1), (2) and (3) are the same as in Example 1. (4) and (5) are mixed solutions of the specified concentrations of the substrate and each inhibitor. The determination method is the same as the method is Example 1. That is to say, the solution of (4) or (5) was added in place of the solution of (3), and the reaction was followed at a determination wave length of 340 nm. The results obtained were that the serum ChE was inhibited by 80% by the addition of dibucaine and by 57.9% by the addition of NaF.

EXAMPLE 6

Method for Determining Serum ChE Activity

| (1) a 250 mM substrate (PCI) solution [prepared by dissolving | 2.0 ml in a 50 mM tris-maleic |
|---|---|
| acid buffer solution (pH 8.2, 25° C.)] | |
| (2) serum or diluted serum | |
| (i) serum I: CONSERA I | 0.1 ml |
| (ii) serum I: CONSERA I | 0.2 ml |
| (iii) serum II: PRECIPATH E | 0.1 ml |

At 37° C., 2.0 ml of (1) was preheated for 2 to 10 minutes, and 0.1 ml or 0.2 ml of the serum or the diluted serum of (2) was added. Each of the mixtures thus obtained was quickly stirred and then placed in a cuvette maintained at 37° C. of a spectroscope, and the decrease of optical absorbance was determined and followed at a determination wave length of 340 nm. The pH of the buffer solution of (1) was adjusted at 25° C. As the sera, CONSERA I (manufactured by Nissui Pharmaceutical Co., Ltd.) and PRECIPATH E (manufactured by Böhringer Mannheim, GmbH.) were used, and the sera were diluted with a 0.877% aqueous sodium chloride solution.

The ChE activity value is calculated from the following equation.

$$IV/liter = \frac{\Delta O.D.^{(1)} \times \begin{pmatrix} \text{Total amount of} \\ \text{reaction solution} \end{pmatrix}}{\begin{pmatrix} \text{Molecular}^{(2)} \\ \text{absorption} \\ \text{coefficient} \end{pmatrix} \times \begin{pmatrix} \text{Amount of} \\ \text{serum} \end{pmatrix}} \times 1000$$

(1) ΔO.D. is a change per minute of optical absorbance at a determination wave length of 340 nm.
(2) The molecular absorption at 340 nm is 2960.

Figure 15:
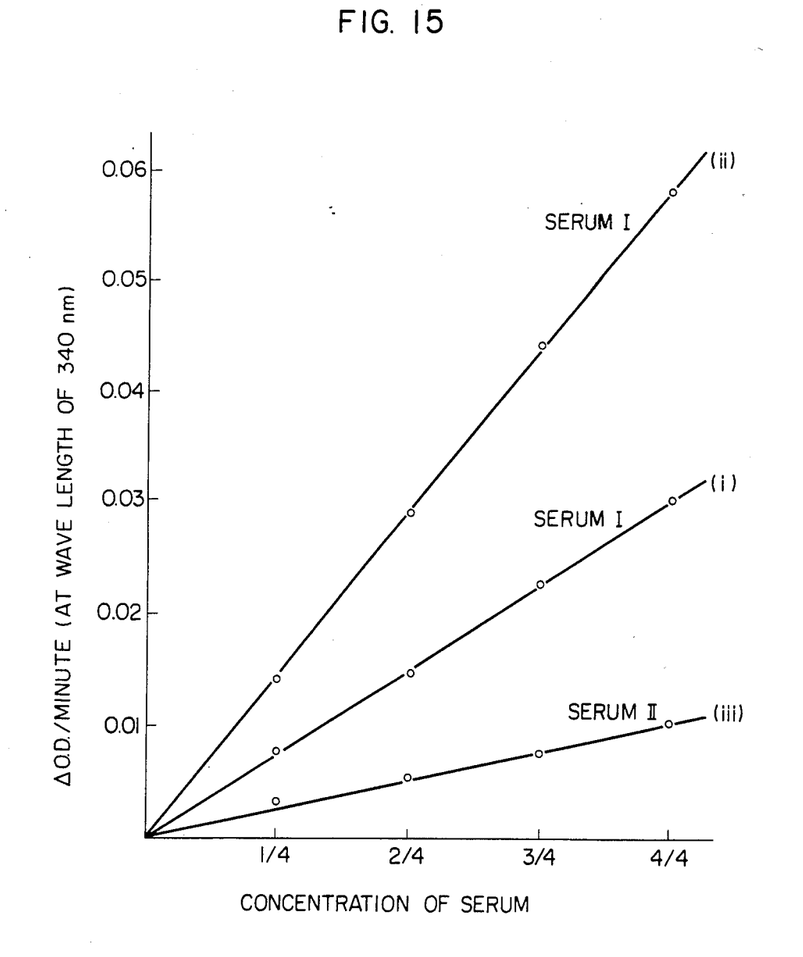
FIG. 15 shows the relationship between diluted serum and enzymatic activity observed for three kinds of sera.

As shown in FIG. 15, for all of the three sera, the serum dilution and the enzyme activity are proportional to each other in the manner of a straight chain passing through the origin very sufficiently.

What is claimed is:

1. A method for determining cholinesterase activity which comprises admixing a solution containing cholinesterase with a substrate, a protocatechuoylcholine halide derivative represented by the general formula (I), wherein X is a halogen atom, and thereafter measuring the optical absorbance of the resulting solution to determine the cholinesterase activity.

2. The method according to claim 1, wherein X in the general formula (I) is an iodine atom.

3. The method according to claim 1, wherein X in the general formula (I) is a chlorine atom.

4. The method according to claim 1, wherein X in the general formula (I) is a bromine atom.

5. The method of claim 1 wherein the optical absorbance is measured at 340 to 360 nm.

6. The method of claim 1 wherein the pH of the solution containing cholinesterase is maintained at from 7.5 to 10 by means of a buffer.

7. The method of claim 6 wherein the buffer is a barbiturate, phosphate, pyrophosphate, glycine, glycylglycine, or tris(hydroxymethyl)aminomethane.

* * * * *